(12) United States Patent
Pelger et al.

(10) Patent No.: US 8,983,627 B2
(45) Date of Patent: Mar. 17, 2015

(54) MEDICAL PROBE FOR ELECTRO-STIMULATION AND BIO-FEEDBACK TRAINING OF PELVIC FLOOR MUSCULATURE

(75) Inventors: Robertus Coenraad Maria Pelger, Oegstgeest (NL); Theodorus Johannes Ouwerkerk, Leiderdorp (NL); Pieternella Johanna Voorham-van der Zalm, Katwijk (NL)

(73) Assignee: Publiekrechtelijke Rechtspersoon Academisch Ziekenhuis Leiden H.O.D.N. Leids Universitair Medisch Centrum, Za Leiden (NL)

( * ) Notice: Subject to any disclaimer, the term of this patent is extended or adjusted under 35 U.S.C. 154(b) by 453 days.

(21) Appl. No.: 12/302,145

(22) PCT Filed: May 23, 2007

(86) PCT No.: PCT/NL2007/050238
§ 371 (c)(1), (2), (4) Date: May 20, 2009

(87) PCT Pub. No.: WO2007/136266
PCT Pub. Date: Nov. 29, 2007

(65) Prior Publication Data
US 2009/0270963 A1    Oct. 29, 2009

(30) Foreign Application Priority Data

May 23, 2006 (EP) .................................. 06114429

(51) Int. Cl.
*A61N 1/04* (2006.01)
*A61N 1/05* (2006.01)
(Continued)

(52) U.S. Cl.
CPC .......... *A61N 1/0524* (2013.01); *A61B 5/04882* (2013.01); *A61N 1/0512* (2013.01);
(Continued)

(58) Field of Classification Search
CPC . A61N 1/0404; A61N 1/0452; A61N 1/0476; A61N 1/0512; A61N 1/0524; A61N 1/36007; A61N 1/36132; A61B 5/04004; A61B 5/0488; A61B 5/04882; A61B 5/04884; A61B 5/20; A61B 5/43; A61B 5/4337; A61B 5/486
USPC ............................... 607/39–41, 138; 600/546
See application file for complete search history.

(56) References Cited

U.S. PATENT DOCUMENTS 3,417,743 A * 12/1968 Carrera ......................... 600/591
3,640,284 A *  2/1972 De Langis .................... 607/71
(Continued)

FOREIGN PATENT DOCUMENTS

DE    199 45 600       3/2001
WO    2005/096926     10/2005

OTHER PUBLICATIONS

International Search Report dated Aug. 30, 2007, from corresponding PCT application.

*Primary Examiner* — Carl H Layno
*Assistant Examiner* — Eugene Wu
(74) *Attorney, Agent, or Firm* — Young & Thompson

(57) ABSTRACT

A probe system for electro-stimulation and bio-feedback training of muscles in the pelvic floor region, in particular for pelvic floor physiotherapy and diagnosis, includes a probe having a probe body which is insertable into a vagina or a rectum, and a plurality of electrodes which are positioned at several locations along the length and around the circumference on the outer surface of the probe, the probe system further includes a control unit, operationally coupled to the probe, adapted for receiving EMG signals from each of the electrodes and for processing each of the signals for mapping the response of the muscles in the pelvic floor region.

33 Claims, 2 Drawing Sheets

(51) Int. Cl.

| | | |
|---|---|---|
| *A61B 5/0488* | (2006.01) | |
| *A61N 1/36* | (2006.01) | |
| *A63B 23/20* | (2006.01) | |
| *A61B 5/00* | (2006.01) | |
| *A61H 19/00* | (2006.01) | |
| *A61H 21/00* | (2006.01) | |
| *A61N 1/08* | (2006.01) | |

(52) U.S. Cl.
CPC ............ *A61N1/36007* (2013.01); *A63B 23/20* (2013.01); *A61B 5/486* (2013.01); *A61H 19/00* (2013.01); *A61H 21/00* (2013.01); *A61N 1/08* (2013.01); *A61H 2205/085* (2013.01); *A61H 19/44* (2013.01); *A61H 2205/086* (2013.01); *A61H 2230/605* (2013.01)
USPC ................. 607/138; 607/39; 607/40; 607/41; 600/546

(56) References Cited

U.S. PATENT DOCUMENTS

| | | | |
|---|---|---|---|
| 3,933,147 A  * | 1/1976 | Du Vall et al. ................ 600/591 |
| 4,224,949 A  * | 9/1980 | Scott et al. .................... 600/373 |
| 4,396,019 A  * | 8/1983 | Perry, Jr. ...................... 600/546 |
| 4,515,167 A  * | 5/1985 | Hochman ..................... 600/549 |
| 5,024,228 A  * | 6/1991 | Goldstone et al. ............ 600/546 |
| 5,452,719 A  * | 9/1995 | Eisman et al. ................ 600/373 |
| 5,662,699 A  * | 9/1997 | Hamedi et al. ................ 607/138 |
| 5,916,172 A  * | 6/1999 | Hodges et al. ................ 600/546 |
| 6,063,045 A  * | 5/2000 | Wax et al. ..................... 600/591 |
| 6,080,118 A  * | 6/2000 | Blythe ........................... 600/591 |
| 6,181,961 B1 * | 1/2001 | Prass ............................. 600/547 |
| 6,185,465 B1 * | 2/2001 | Mo et al. ....................... 607/138 |
| 6,356,777 B1 | 3/2002 | Garfield et al. |
| 6,741,895 B1 | 5/2004 | Gafni et al. |
| 2003/0083590 A1* | 5/2003 | Hochman et al. ............. 600/549 |
| 2004/0054392 A1* | 3/2004 | Dijkman ....................... 607/138 |
| 2004/0068203 A1* | 4/2004 | Gellman et al. ............... 600/587 |
| 2004/0122341 A1* | 6/2004 | Walsh et al. ................... 600/591 |
| 2005/0085869 A1* | 4/2005 | Tehrani et al. ................. 607/42 |
| 2005/0182456 A1* | 8/2005 | Ziobro et al. ................... 607/48 |
| 2006/0036188 A1* | 2/2006 | Hoffman et al. .............. 600/591 |
| 2008/0001735 A1* | 1/2008 | Tran ......................... 340/539.22 |

* cited by examiner

MEDICAL PROBE FOR ELECTRO-STIMULATION AND BIO-FEEDBACK TRAINING OF PELVIC FLOOR MUSCULATURE

BACKGROUND OF THE INVENTION

The invention relates to probes used in intra vaginal- and/or intra anal electro-stimulation and bio-feedback training, in particular for registering and training the pelvic floor muscles, the urethral sphincter and the internal and external anal sphincters. Also the probes will be used for the aim of research.

In particular, these probes are used in an inserted position into the vagina or into the rectum, i.e. intravaginal or intra-anal.

Many such a probes are known in practice. One of the first of such probes is the so-called manometric probe, which is used as a perineometer by Kegel and described in AM J. obst Gyneocol. 1948; 65; pages 238-304. Since the introduction of this probe, many electrodes have been developed for intra-vaginal and intra-anal electro stimulation and bio feedback training in the treatment of pelvic floor.

Intravaginal and intra-anal electro stimulation and bio feedback training are used for treatment of urinary urge- and stress incontinence, anal dysfunction, and sexual dysfunction. For optimal treatment, knowledge of the structures that are the main targets in stimulating and bio feedback training is needed.

This knowledge of both the anatomy of the pelvic floor and physiological aspects should result in optimal design of probes. Differences in inter-human anatomy are a challenge. Many of the currently used probes, however, have been developed empirically.

Based on the present knowledge of the inventors, the pelvic floor basically comprises the levator ani and the puborectal muscle. The pelvic floor muscle contraction presumably involves contraction of these two muscles. The levator ani is a muscle active in the process of evacuation. On contraction it facilitates the process of defecation and micturition. In contrast, the puborectal muscle is a muscle active in the process of continence. The puborectal muscle is a vertical lying U-shaped sling embracing the urethra and anal channel. Furthermore, the external anal and urethral sphincters originate in the puborectal muscle. During puborectal muscle contraction, the two sphincters contracts synchronously, resulting in a closure (sealing) of the urethra and anal channel.

Continence, in short, is a result of the direct action of the puborectal muscle per sé and the external anal and urethral sphincters.

In sphincter/stress incontinence, enforcement of the external sphincters, and/or pelvic floor muscles, the puborectal muscle should, according to the inventors, be the main target of electro stimulation. However, the primary targets should not be the muscles but the pelvic and/or pudendal nerve fibres. These fibres directly activated by electro stimulation indirectly induce activity of the muscles.

In urge incontinence, two modes of action are described: stimulation of pudendal nerve afferents, resulting in detrusor inhibition through central reflexes, as well as stimulation of efferents resulting in enhancement of pelvic floor and urethral sphincter musculature tone, inducing detrusor inhibition through the guarding reflex. As these modes of action are quite different, with different targets, it is questionable whether the demands for optimal probes are uniform. It is more likely that various types of probes may be needed for optimal stimulation treatment as well as for bio feedback registration.

Various commercially available probes, positioned according to standard protocol as used in daily practice by pelvic floor physiotherapists, were studied and evaluated.

To investigate the positioning of the anal and vaginal probes, we used the Aloka® SSD 1700 Ultrasound, the power Doppler and the Falcon Ultrasound scanner Type 2101 from Bruel-Kjaer Medical, with transducer type 8658/S and 1850, to localize musculature and the neurovascular bundle of the pelvic floor. The transducer 8658/S was used in combination with the Brachy balloon from Barzell Whitmore Maroon Bells®. The anatomy of the pelvic floor was investigated in detail using the 0.5-T MRI scanner (Philips NT5, Philips Medical Systems®, Best, the Netherlands) equipped with an endoanal coil. We performed a thorough literature review on pelvic floor anatomy and placements of probes in pelvic floor physiotherapy. We evaluated the optimal placement of probes in two healthy multiparous women, without pelvic floor dysfunction. The distance from the recording rings to the muscles is described at the proximal parts of the puborectal muscle and the anal external sphincter. Positioning of the anal probes was examined in left lateral decubitis position, with the ultrasound transducer introduced in the vagina. The positioning of the vaginal probes was examined in lithotomic position with the ultrasound transducer in the anal canal. The anatomy was compared with a vast number of MRI examinations performed with an endoanal coil according to protocol in our institute. During the examination the women were asked to strain and to bear down. Repeated measures were performed on both subjects with a time interval of three weeks. The time elapsed between using each test probe was 15 min and we requested both women to do 10 fast twitch contractions and 5 slow twitch contractions. Five probes, 3 vaginal and 2 anal, were tested and technically described. Three probes have longitudinal recording plates and two have concentric recording plates.

The Neen vaginal probe from Verity Medical Ltd® has a total length of 7.5 cm and a circumference of 10 cm. It has two longitudinal recording plates. The distance between the top of the probe and both recording plates is 1.5 cm. The two recording plates are situated alongside the body of the probe and are 1.5 cm wide and 3.5 cm long. The distance of the base of the probe to both recording plates is 3.0 cm. The probe is inserted into the vagina, up to the ring at the introitus.

The Veriprobe vaginal probe with longitudinal plates from Verity Medical Ltd® has a total length of 8.8 cm and a circumference of 8.2 cm. Two longitudinal rectangle-shaped recording plates are situated alongside the body of the probe and are 2.0 cm wide and 3.5 cm long, and are flush with the body of the probe. The distance between the two recording plates is 2.0 cm. The distance of the recording plate to the top is 1.5 cm, to the bottom 2.1 cm. The external part of the probe is 1.3 cm long. This probe is inserted up to its handle at the introitus.

The EMG 2-ring vaginal probe 2 mm from V.M.P. Bioparc® has two circular recording plates. The total length of this probe is 12.7 cm, the circumference 7.7 cm. The distance from the top ring to the top of the probe is 1.4 cm. The distance between the two rings is 1.8 cm and the width of both rings is 1.0 cm. This probe is inserted up to the thinnest part, at the level of the introitus.

The Neen anal probe, anuform, from Verity Medical Ltd® has a total length of 8.4 cm and a maximal circumference of 7.0 cm. It consists of a body, with two longitudinal recording plates, a neck and an open ring. The recording plates are trapezoid like. The distal side of the recording plate is 0.5 cm wide, the proximal side 1.0 cm. The length of the recording plate is 2.7 cm. The distance between the two recording plates is about 2.0 cm. The distance of the recording plate to the top of the probe is 1.0 cm, to the base 0.5 cm. The length of the ring is 3.0 cm. This probe is inserted with the ring up to the anal verge.

The EMG 2-ring anal probe 2 mm from V.M.P. Bioparc® has two circular recording plates. The probe has a total length of 13.6 cm. The circumference of the top of the probe is 5.0 cm. The distance from the distal recording ring to the top is 1.8 cm. The distance between the two rings is 1.0 cm. The width of both rings is 0.5 cm. The distance from the proximal ring to the next bulge is 1.0 cm. There are three bulges with two gaps of 1.0 cm in between. These bulges are for the purpose of fixation. The distance from the proximal bulge to the base of the probe is 6.0 cm. This probe is inserted with the proximal bulge at the anal verge.

The literature on the topic of type of probes of the current invention is scarce. The commercially available probes studied vary in design, that is in shape and size of the body of the probe and in type of recording electrodes (plates or rings). Notwithstanding, they all have the same purpose: proper placement during treatment of pelvic floor dysfunction. What proper placement means depends on the structures that need to be stimulated or registered (nerves, external sphincters, puborectal muscle, or other pelvic floor muscles). The muscular anatomy can be described as consisting of, roughly speaking, 3 layers of muscles: from caudal to cranial: the anal external sphincter, the puborectal muscle, and the levator group. The results of the measurements of the vaginal electrodes vary from close to the puborectal muscle (Veriprobe) to 6 cm cranial of the puborectal muscle (EMG 2-ring vaginal probe 2 mm). The anal electrodes vary from next to the anal external sphincter, 1 cm caudal of the puborectal muscle (Neen probe, anuform), to 2 cm cranial of the puborectal muscle and 4 cm cranial at the anal external sphincter (EMG probe anal, 2 rings). Measurements were reproducible in each subject and for each probe, independently of the sequence. Readings of the probe were not influenced by the presence or absence of the ultrasound probe in the adjacent orifice. In case of electrostimulation for treatment of urinary urge incontinence, stimulating should be focused on afferent nerve fibers of the plexus pelvicus and the pudendal nerve or, if the guarding reflex is involved as well, as in case of stress incontinence, on the external sphincter and pelvic floor musculature. It is assumed that, in this respect, of all pelvic floor muscles, the puborectal muscle is the most relevant one. Using electrostimulation in cases of fecal incontinence, the focus is on the anal external sphincter as well as on the puborectal muscle. In biofeedback training we aim to record the function of the urethral and anal sphincters and the puborectal muscle. It was found that for biofeedback training a close relation between the electrode plates and the muscle itself is important. However, in cases of electrostimulation of pelvic floor dysfunction (stress and urge incontinence, fecal incontinence, and obstructed defecation), stimulation of afferent and/or efferent nerves is found to be mandatory and not necessarily direct stimulation of the involved muscles. The general requirement to obtain an effect of electrical stimulation, found during our study, is that the intensity of stimulation should be sufficient to elicit impulses in a relevant nerve. The threshold intensity varies inversely with the nerve fiber diameter, the distance between the nerve and the size of the stimulating electrode, and the pulse configuration. All tested probes had a large electrode area. The effect of this is that a relatively large current is needed to elicit an effect, but this is not by itself harmful. If the electrodes are not positioned at the anal external sphincter and/or the puborectal muscle, we assume that in biofeedback training we are in fact registering a composite EMG signal of the total area, not only the pelvic floor, but the sum of all active surrounding muscles as well as the response to intra-abdominal pressure. Based on our findings we conclude that the electrodes of the probes, as we use them now during electrostimulation and biofeedback training in the treatment of pelvic floor dysfunction, are not optimal for the structures we want to stimulate or to register. Observation of the anal positioning of the probe by vaginal ultrasound demonstrated that during an attempt to perform a pelvic floor contraction, the anal external sphincter 'rolls' backwards, taking the shape of a 'drop'. Simultaneously the urethra stretches itself, elongates and is pulled down during contracting the urethral sphincter and the puborectal muscle. In contrast, during straining, the urethra is shortened and moves upwards.

Optimal probe fitting may be even more complex. According to one reference, sex-dependent differences are visible in all three planes. Because of the clear difference in male and female anatomy, different electrodes are needed in the treatment of pelvic floor dysfunction. Ultrasound and MRI imaging demonstrated that the positioning of the electrodes is close to the plexus pelvicus. Besides stimulation of afferent or efferent, motoric nerves, the mode of action of intravaginal stimulation for urge incontinence may also be related to direct stimulation of the bladder wall or the urethra. If we position the electrodes at the anal external sphincter or in the anal canal below the linea dentata, or just behind the vaginal introitus, electrostimulation is far too painful for the patient. Direct stimulation of skin and mucosa, also at lower intensity, is probably the cause of this pain sensation. In case of biofeedback, the optimal position of the probes for stimulation is quite different. In our opinion the ideal probe should be:

1. registering;
    vaginal: the puborectal muscle, the external urethral sphincter;
    anal: the puborectal muscle, the anal external sphincter, the levator ani;
2. stimulating the structures we want to stimulate: nerves or muscles;
3. shaped and sized adapted to the local anatomy (not vice versa);
4. comfortable for the patient;
5. maintaining its position;
6. the reference electrode should be incorporated;
7. suitable for sterilization;
8. durable;
9. containing rings and plates of electrodes.

CONCLUSIONS

As the five examined commercially available probes vary considerably in their relationship with the, roughly speaking, three layers of muscles, it is unlikely that they are all fit for optimal use. In our opinion, the anal and vaginal probes we presently use have a too large diameter, even in women after vaginal delivery.

U.S. Pat. No. 6,741,895 discloses a vaginal probe for stimulation of the nerves of the vagina in order to do research on and possibly treat sexual dysfunction in women. In one of the embodiments, a probe may have an array of selectively excitable sub-elements, for instance for vibrational stimulation. The stimulation is controlled using a computer, and a subject may respond verbally.

U.S. Pat. No. 6,356,777 discloses a probe for treatment of muscle cells and nerves of the uterus and cervix using electrical pulses for preventing preterm labour. The probe can have a form which penetrates the walls of the uterus, cervix or vagina, or may have a form which is insertable into the vagina. The insertable probe has annular electrodes which are well known, for instance from commercially available probes described above.

WO-2005/096926 discloses a sensor for detecting myo-electrical signals originating from sphincters and which for this purpose has electrodes which are organized in several rings of electrodes around the probe surface.

SUMMARY OF THE INVENTION

An object of the current invention is to obviate at least part of the drawback of current probes.

Another object of the invention is to provide a probe which can be used for both measuring and electro-stimulation.

Another object of the invention is to provide a probe which is comfortable to use.

Yet another object of the invention is to provide a probe which can be used for several therapeutic purposes and several diagnostic purposes relating to medical problems indicated above.

Yet another object is to provide a probe which can be used both intravaginal and intra-anal.

Another object is to provide a probe which can selectively stimulate muscles and/or nerves.

Yet another object of the invention is to provide a probe which has a shape which is adapted to the physiological properties of various persons.

To this end, the invention provides a probe system for electro-stimulation and bio-feedback training of muscles in the pelvic floor region, in particular for pelvic floor physiotherapy and diagnosis, said probe system comprises a probe having a probe body which is insertable into a vagina or a rectum, and a plurality of electrodes which are positioned at several locations along the length and around the circumference on the outer surface of said probe, said probe system further comprises a control unit, operationally coupled to said probe, adapted for receiving EMG signals from each of said electrodes and for processing each of said signals for mapping the response of the muscles in the pelvic floor region.

By providing electrons at various locations both along the length and the circumference of the probe, it has become possible to determine the exact location of regions which have to be treated or trained. Furthermore, stimulation can be given to those exact locations. In many case, it was found that the pelvic floor muscles need to be trained in order to overcome or treat incontinence problems, and not or not only the sphincters. In fact, for most patients stimulation of the sphincters is unpleasant. Using mapping software, a map of muscle activity is provided. This map may be 2D, but in order to identify muscle activity it is preferred to provide a 3D map of the muscle activity.

Further embodiments of the current invention are described in the depending claims and in the description below.

In an embodiment of the probe of the invention, said electrodes comprise patch-shaped electrodes.

In an embodiment of the probe of the invention, said electrodes are located on said outer surface in a regular matrix pattern.

In an embodiment of the probe of the invention, said electrodes are grouped in several rings on said surface around said probe.

In an embodiment of the probe, said electrodes are grouped in several longitudinal rows on said surface of said probe.

In an embodiment of the probe of the invention, said electrodes are grouped in several longitudinal rows on said surface of said probe and each row of electrodes is separately usable.

In an embodiment of the probe of the invention, said electrodes are grouped in several rings on said surface around said probe and each ring of electrodes is separately usable.

In an embodiment of the probe of the invention, said electrodes are unipolar electrodes for detecting EMG unipolar signals and applying at least one electrical signal to the muscular layer In an embodiment of the probe of the invention, said electrodes have an stainless steel electrode surface.

In an embodiment of the probe of the invention, said probe body mainly comprises non-conductive material, preferably synthetic material which is bio-compatible.

In an embodiment of the probe of the invention, said probe is substantially rod shaped, preferably said probe substantially is a rigid rod. Preferably, the rod-shaped main body will be made of a non-conductive polymeric material. Such a probe will in most cases be moulded, specifically in such a way that the electrodes and wiring will be incorporated into the polymeric material and the main body will be solid. Preferably, a polymeric material is used which feels well when inserted, and is easy to clear. Suitable polymeric materials are well known to a person skilled in the art.

In an embodiment of the probe of the invention, said probe has a rounded tip.

In an embodiment of the probe of the invention, said electrodes are grouped into at least 6 groups of at least 4 electrodes each.

In an embodiment of the probe of the invention, said probe is operationally coupled to a control unit.

In an embodiment of the probe of the invention, each electrode is wire-coupled to said control unit.

In an embodiment of the probe of the invention, wherein said wires exit said probe at the rear side of said probe. In order to facilitate easy handling of said probe and to insure accurate and reproducible measurement results, the probe may be provided with a stop for determining the insertion depth of the probe. Such a stop may be provided in the form of a ring positioned near the rear end of the probe. In a specific embodiment, the longitudinal positional of this ring on the probe may be adjustable. Furthermore, in an embodiment the rear end of the probe may be thickened. In such an embodiment, the optional ring or stop will be provided before the thickened portion.

In an embodiment of the probe of the invention, said the location of each electrode on said probe is stored in said control unit.

In an embodiment of the probe of the invention, said control unit comprises a measurement unit for obtaining measurement signals from said electrodes.

In an embodiment of the probe of the invention, said measurement unit is adapted for measuring signals from each electrode separately.

In an embodiment of the probe of the invention, said control unit comprises an activation unit for applying electrical signals on said electrodes for influencing selected muscles, nerves, or part of said selected muscles or nerves, in said pelvic floor region. The electrodes may be activated ringwise, or one or more longitudinal rows of electrodes may be activated together. In most cases, however, each electrode will receive its own individual signal.

In an embodiment of the probe of the invention, said activation unit is adapted for applying electric signals based upon measurement signals from said measurement unit.

The invention further relates to a method for electro-stimulation and bio-feedback training of muscles in the pelvic floor region, in particular for pelvic floor physiotherapy and diagnosis, using the probe according to any one of the preceding claims, comprising the steps of:

determining electric signals from muscles or nerves in the pelvic floor region using said electrodes, and based upon said determined electric signals, applying electric signals to said electrodes for causing contraction en relaxation of muscles of part of these muscles in the pelvic floor region.

Using the probe of the invention in this way, it is possible to determine the status and condition of specific muscles, and to provides each muscle with its specific stimulation. This has become possible by not only activation each electrode individually, but additionally determining the specific shape and strength of each electrode and determining it in relation to the signals on the other electrodes.

In an embodiment of the method, it comprises the further steps of:

measuring electric signals from muscles or nerves in the pelvic floor region using said electrodes;

determining muscular tension of said muscles in the pelvic floor region from said electric signals, and based upon said calculated muscular tension, applying electric signals to said electrodes for causing contraction and/or relaxation of selected muscles or part of said muscles in said pelvic floor region.

The invention furthermore relates to a computer program product which, when working on a control unit for controlling the probe according to any one of the preceding claims, causes said control unit to perform the step of:

reading electric signals from each of said electrodes;

calculate muscular tension in muscles in said pelvic floor region from said electric signal;

calculate electric signals to be applied to each electrode;

control said probe for applying said calculated electric signals to said electrodes.

SHORT DESCRIPTION OF THE DRAWINGS

An embodiment of the current invention is described in detail below and shown in the accompanying drawings, in which.

DESCRIPTION OF EMBODIMENTS OF THE INVENTION

Figure 1:
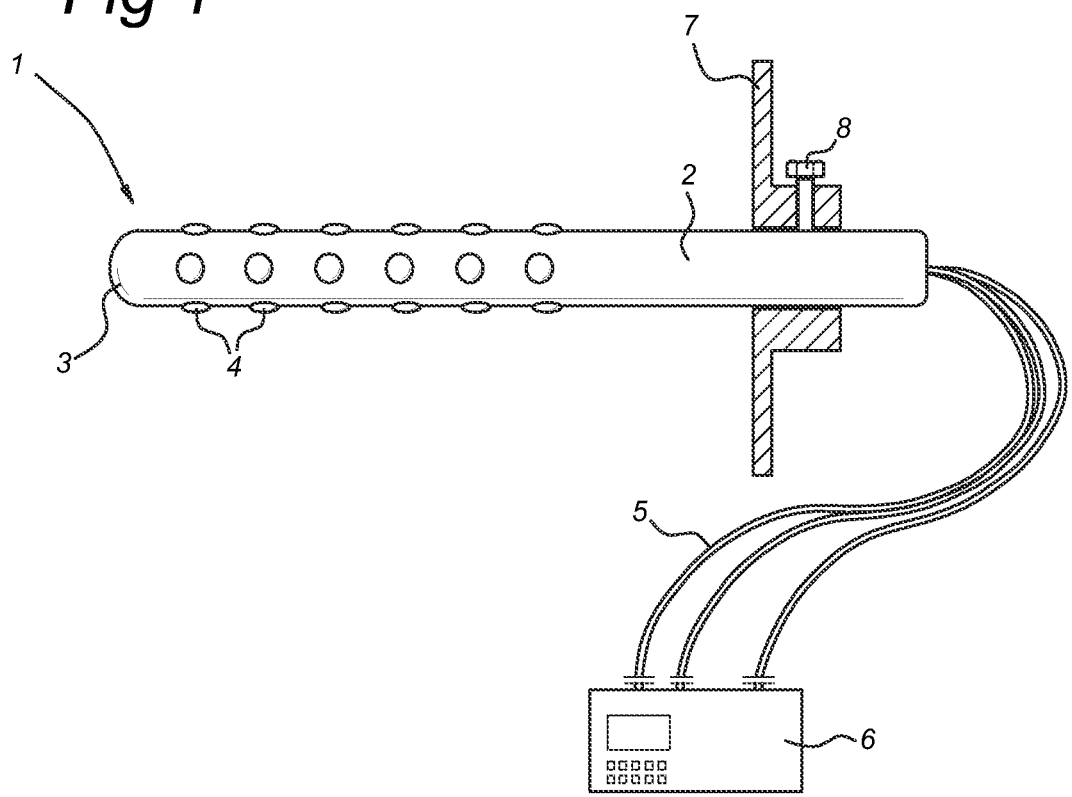
FIG. 1 shows a probe according to the current invention with control unit.

FIG. 1 shows a possible embodiment of a probe 1 of the current invention. This probe 1 has a rod shape body 2. The dimensions of this probe 1 have been chosen in such a way that in can be used with different persons, man and women, that it can be used both intravaginal and intra-anal. To that end, its diameter should be about 1-2 cm. The probe has a plurality of electrode patches 4, located at both the length and circumference of the probe. The length of the probe covered with the electrodes preferably is about 10-15 cm.

Furthermore, the probe has a rounded tip 3, and the probe 1 extends beyond the electrodes 4 in order to make it possible to handle the probe once it is inserted.

For reproducible placement of the probe and keeping it in place during use, the probe 1 has a circumferential stop surface 7. It is slidable over the probe 1 and is provided with a fixation means 8 for fixing its position on the probe 1. In this embodiment a fixation screw, for fixing its position on the probe 1 is provided. The stop surface 7 in this embodiment is a disk. This stop functions both as stop for determining the insertion depth of the probe 1, but also as a fixation means for fixing its position. To that end, in use, its circumferential edge is clamped between the upper legs or in the groin of a patient.

In this embodiment, the electrodes 4 are wire-coupled using wires 5 to a control unit 6. This control unit 6 can be a general purpose computer provided with software for reading electric signals from each of the electrodes 4, and for applying adjustable electric signals to selected electrodes. Furthermore, this software may be able to store the electric signals which were read in memory provided in the computer, and to store settings corresponding to the electrodes selected to be activated as well as the strength, duration and possibly pulse shape applied to the electrodes.

In a preferred embodiment, the control unit reads electric signals, for instance after a person is instructed to activate certain muscles, subsequentially it calculates an activation program based upon the measured values and possibly a selected treatment program which was input by a therapist of physician, applies calculated signals to selected electrodes, and in between activation or after activation, again read electric signals from each of the electrode and calculates the effect of these signals for providing feedback to the therapist of physician. If needed, the therapist of physician can modify the settings, or the control unit can adjust its settings based upon the readings and apply modified or adjusted signals to the same or different electrodes.

Figure 2:
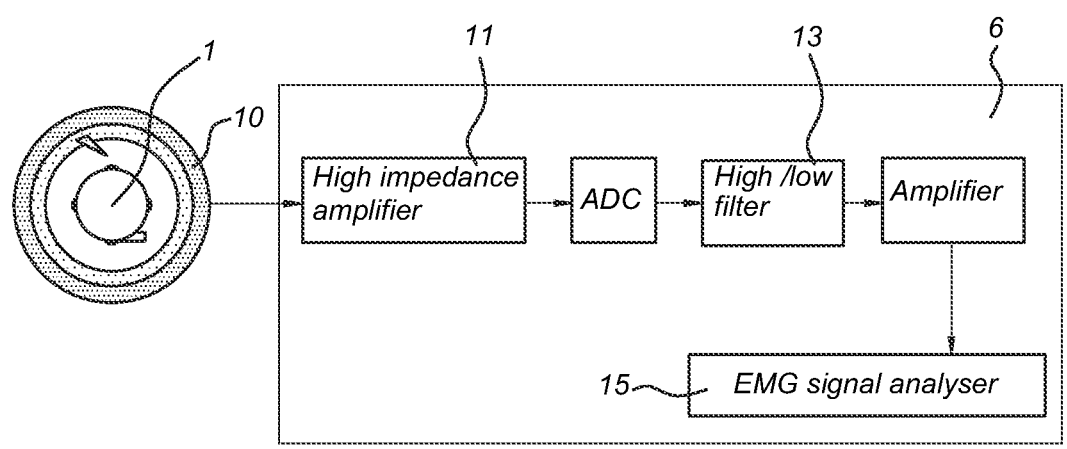
FIG. 2 shows a pathway of signal processing using the probe of FIG. 1.

FIG. 2 shows the probe 1 in use, surrounded by a muscular layer 10 giving EMG signals, in the control unit diagnostic phase. The electric signal is processed by a high impedance amplifier 11, converted into a digital signal using a 24 bits ADC, and filtered using a high/low filter 13.

After this, the signal is processed using a EMG signal analysis unit 15 which is know per sé to a person skilled in the art. In fact, each electrode 4 will result in an EMG signal. As the electrodes are unipolar electrodes, the signals can be used as absolute values. It is also possible to calibrate these signals against the values of one or more other electrodes 4, or use another reference for that purpose. Using the control unit 6, it is also possible to functionally couple several electrodes to one another, for instance in rings or longitudinal plates, but better yet in a configuration adapted to the measurement results.

Using mapping software, a 3D map of muscular activity can be constructed using the signals from all or part of the electrodes 4.

Figure 3:
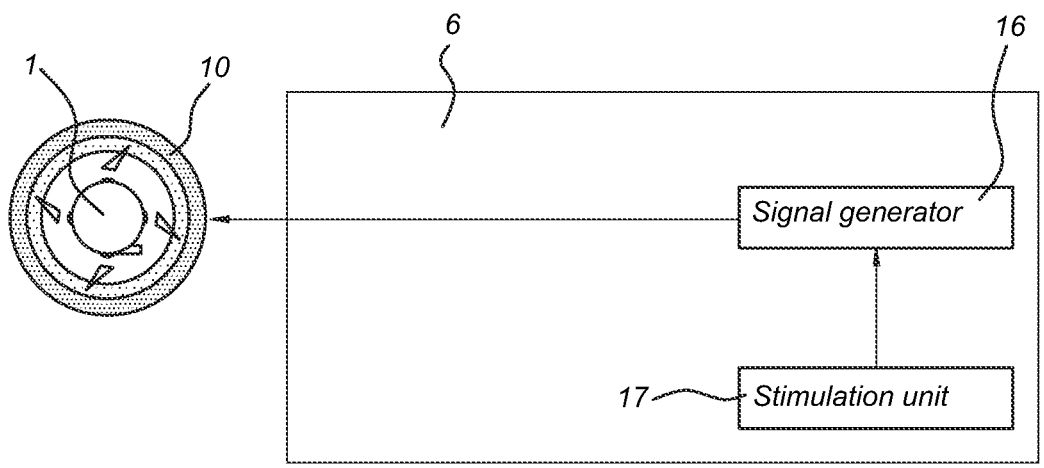
FIG. 3 shows a pathway of electrical stimulation and treatment using the probe of FIG. 1.

FIG. 3 shows the probe 1 in used, again surrounded by the muscular layer 10, in the therapeutic phase. In this phase, the stimulation unit 17 calculates the electric signal which has to be given by each electrode 4. The stimulation unit 17 controls generator 16 which generates the signal (shape, strength, duration, pattern) for each electrode.

It is to be understood that the above description is included to illustrate the operation of the preferred embodiments and is not meant to limit the scope of the invention. The scope of the invention is to be limited only by the following claims. From the above discussion, many variations will be apparent to one skilled in the art that would yet be encompassed by the spirit and scope of the present invention.

The invention claimed is:

1. A method for bio-feedback training of muscles in the pelvic floor region, or for pelvic floor physiotherapy using a probe system that comprises a probe having a probe body inserted into a vagina or a rectum, a plurality of uni-polar electrodes which are positioned at several locations along the length and around the circumference on the outer surface of said probe thereby defining an electrode matrix pattern, and a control unit operationally coupled to said probe and adapted for receiving absolute value electromyography (EMG) signals from each of said electrodes and for processing each of said absolute value EMG signals for mapping the response of the muscles in the pelvic floor region,
the method comprising the steps of:
determining muscle tension in the pelvic region based on the absolute value EMG signals measured with the electrodes;
providing bio feedback based on said muscle tension; and
repeating these steps in the bio-feedback training for pelvic floor physiotherapy.

2. The method according to claim 1, further comprising the steps of:
calculating electric stimulus signals to be applied to the electrodes based on the determined muscular tensions from the absolute value EMG signals only, and
controlling the probe to apply the calculated electric stimulus signals to the electrodes causing at least one of contraction and relaxation of the muscles in the pelvic floor region.

3. A probe system for electro-stimulation and bio-feedback training of muscles in the pelvic floor region, or for pelvic floor physiotherapy and diagnosis, said probe system comprising:
a probe having a probe body which is insertable into a vagina or a rectum;
a plurality of uni-polar electrodes arranged in a matrix and which are positioned at several locations along the length and around the circumference on the outer surface of said probe, each electrode being configured to measure absolute value electromyography (EMG) measurements;
a control unit, operationally coupled to said probe, adapted for receiving absolute value EMG signals from each of said electrodes and for processing each of said absolute value EMG signals for mapping the response of the muscles in the pelvic floor region,
wherein the control unit is configured to:
determine muscle tension in the pelvic region based on absolute value measurement signal values measured with the electrodes,
provide bio-feedback based on said muscle tension, and
repeat these steps in a training for pelvic floor physiotherapy.

4. The probe system according to claim 3, wherein the control unit is further configured to:
calculate electric stimulus signals to be applied to the electrodes based on the determined muscular tensions, and
control the probe to apply the calculated electric stimulus signals to the electrodes causing at least one of contraction and relaxation of the muscles in the pelvic floor region.

5. A computer program product embodied in a non-transitory tangible medium which, when working on the control unit for controlling the probe system according to claim 3, configures said control unit to:
control the uni-polar electrodes for obtaining measurement signal values;
read the electric signals from each of said uni-polar electrodes;
calculate the muscular tension in the muscles in said pelvic floor region from said electric signals; and
provide bio-feedback based on the determined muscular tension.

6. The computer program product according to claim 5, wherein the program further configures the control unit to:
calculate the electric stimulus signals to be applied to each of the electrodes; and
control said probe to apply said calculated electric stimulus signals to respective said electrodes.

7. A probe system for electro-stimulation and bio-feedback training of muscles in the pelvic floor region, in particular for pelvic floor physiotherapy and diagnosis, said probe system comprising:
a probe having a probe body which is insertable into a vagina or a rectum, and a plurality of uni-polar surface electrodes which are positioned, in a matrix, at several locations along the length and around the circumference on the outer surface of said probe, the probe being configured to measure absolute value electromyography (EMG) electrode measurements;
a control unit, operationally coupled to said probe, adapted for receiving only absolute value EMG signals from each of said electrodes and for processing each of the absolute value EMG signals for mapping the response of the muscles in the pelvic floor region,
wherein the control unit is configured to:
(1) determine the absolute value electric signals from muscles or nerves in the pelvic floor region using the uni-polar electrodes,
(2) determine muscular tension of the muscles in the pelvic floor region from the determined absolute value electric signals,
(3) calculate electric stimulus signals to be applied to the electrodes based on the determined muscular tensions,
(4) control the probe to apply the calculated electric stimulus signals to the electrodes causing at least one of contraction and relaxation of the muscles in the pelvic floor region, and
(5) provide bio-feedback on the determined muscular tension,
wherein the control unit is configured to control the uni-polar electrodes for obtaining electrical signals providing measurement of the absolute values.

8. The probe system of claim 7, wherein said electrodes comprise patch-shaped electrodes, located on said outer surface in a regular matrix pattern, wherein said electrodes are grouped in several rings on said surface around said probe and are grouped in several longitudinal rows on said surface of said probe, and wherein the distance between adjacent electrodes in said rings and rows is similar to or larger than the size of the electrodes measured in the same direction and wherein each ring of electrodes is separately usable and/or wherein each row of electrodes is separately usable.

9. The probe system according to claim 8, wherein said electrodes have an electrode surface and said probe body comprises non-conductive material between said electrodes, the electrode surfaces extending above the surface of the probe body, wherein said probe is substantially rod shaped and has a rounded tip, free of electrodes.

10. The probe system of claim 9, wherein the electrodes have a convex surface.

11. The probe according to claim 7, wherein said probe further comprises a stop surface for setting the insertion depth of the probe.

12. The probe of claim 11, wherein said probe further comprises a fixation means for fixing an inserted position of the probe in use.

13. The probe according to claim 7, wherein each electrode is wire-coupled to said control unit.

14. The probe according to claim 13, wherein said wires exit said probe at a rear side of said probe.

15. The probe according to claim 7, wherein said control unit comprises an activation unit for applying the electric stimulus signals to said electrodes for influencing selected muscles, nerves, or part of said selected muscles or nerves, in said pelvic floor region.

16. The probe according to claim 15, wherein said control unit comprises a measurement unit for obtaining measurement signals from said electrodes, and wherein said activation unit is adapted for applying electric stimulus signals based upon measurement signals from said measurement unit.

17. The probe system of claim 7, wherein said electrodes comprise patch-shaped electrodes.

18. The probe system according to claim 7, wherein said electrodes are located on said outer surface in a regular matrix pattern.

19. The probe system according to claim 7, wherein said electrodes are grouped in several rings on said surface around said probe.

20. The probe system according to claim 7, wherein said electrodes are grouped in several longitudinal rows on said surface of said probe.

21. The probe system according to claim 7, wherein said electrodes are grouped into at least 6 groups, each of at least 4 electrodes in a ring.

22. The probe system according to claim 7, wherein said electrodes are grouped in several longitudinal rows on said surface of said probe and wherein each row of electrodes is configured to be activated separately.

23. The probe system according to claim 7, wherein said electrodes are grouped in several rings on said surface around said probe and wherein each ring of electrodes is configured to be separately usable.

24. The probe system according to claim 7, wherein said electrodes have a stainless steel electrode surface.

25. The probe system according to claim 7, wherein said probe body comprises non-conductive material.

26. The probe system according to claim 7, wherein said probe is substantially rod shaped.

27. The probe system according to claim 7, wherein the probe body is substantially cylindrical having a diameter between 1 and 2 cm.

28. The probe system according to claim 7, wherein said probe has a rounded tip.

29. The probe according to claim 7, wherein said location of each electrode on said probe is stored in said control unit.

30. The probe according to claim 7, wherein said control unit is adapted for measuring signals from each electrode separately.

31. The probe system according to claim 7, further comprising a bio feedback representation device.

32. A method for electro-stimulation and bio-feedback training of muscles in the pelvic floor region, or for pelvic floor physiotherapy and diagnosis, using the probe system according to claim 7, comprising the steps of:
  determining the electromyography (EMG) signals from the muscles or nerves in the pelvic floor region using said electrodes, wherein the electric signals are determined by using the electrodes as uni-polar electrodes;
  determining the muscular tension of the muscles in the pelvic floor region from the determined EMG signals only;
  calculating the electric stimulus signals to be applied to each of the electrodes based on the determined muscular tension;
  controlling said probe to apply said calculated electric stimulus signals to said electrodes; and
  providing bio-feedback based on the determined muscle tension.

33. A computer program product embodied in a tangible non-transitory medium which, when working on the control unit for controlling the probe system according to claim 7, causes said control unit to perform the step of:
  controlling said electrodes as uni-polar electrodes for obtaining measurement signal values;
  reading the electromyography (EMG) signals from each of said electrodes, said electrodes being configured to measure absolute value EMG measurements;
  calculating the muscular tension in the muscles in said pelvic floor region from said absolute value EMG signals;
  calculating the electric stimulus signals to be applied to each of the electrodes;
  controlling said probe to apply said calculated electric stimulus signals to respective said electrodes; and
  providing bio-feedback based on the determined muscle tension.

* * * * *